(12) United States Patent  
Liu

(10) Patent No.: US 9,420,831 B2  
(45) Date of Patent: *Aug. 23, 2016

(54) ELECTRONIC CIGARETTE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 695 days.

This patent is subject to a terminal disclaimer.

(21) Appl. No.: 13/914,277

(22) Filed: Jun. 10, 2013

(65) Prior Publication Data

US 2014/0299140 A1 Oct. 9, 2014

(30) Foreign Application Priority Data

Apr. 3, 2013 (CN) ...................... 2013 2 0165796 U

(51) Int. Cl.
*A24F 47/00* (2006.01)
*A61M 15/06* (2006.01)

(52) U.S. Cl.
CPC .............. *A24F 47/008* (2013.01); *A61M 15/06* (2013.01)

(58) Field of Classification Search
None
See application file for complete search history.

(56) References Cited

U.S. PATENT DOCUMENTS

| | | | | |
|---|---|---|---|---|
| 5,147,582 | A * | 9/1992 | Holzner, Sr. ............ | A61L 9/122 239/60 |
| 6,443,146 | B1 * | 9/2002 | Voges .................... | A24F 47/002 128/200.14 |
| 2013/0180533 | A1 * | 7/2013 | Kim ....................... | A24F 47/008 131/273 |
| 2013/0192615 | A1 * | 8/2013 | Tucker ................... | H01C 17/00 131/328 |

* cited by examiner

*Primary Examiner* — Michael H Wilson
*Assistant Examiner* — Eric Yaary
(74) *Attorney, Agent, or Firm* — Tim Tingkang Xia, Esq.; Locke Lord LLP

(57) ABSTRACT

This invention relates to an electronic cigarette, comprising an atomizer and a battery pipe; an end of the atomizer is connected to a sucking mouth component, a battery chamber is mounted in the atomizer, and the battery pipe is fixedly inserted in the battery chamber; the atomizer also includes an atomizing core component detachably configured between the battery pipe and the sucking mouth component. By implementing the electronic cigarette of the invention, it is convenient in carrying, and the atomizing core component is replaceable, and convenient to use.

13 Claims, 7 Drawing Sheets

ELECTRONIC CIGARETTE

CROSS-REFERENCE TO RELATED APPLICATIONS

This non-provisional application claims priorities under 35 U.S.C. §119(a) on Patent Application No. 201320165796.7 filed in P.R. China on Apr. 3, 2013, the entire contents of which are hereby incorporated by reference.

FIELD OF THE INVENTION

This invention relates to the field of electronic heated product, and more particularly to an electronic cigarette.

BACKGROUND OF THE INVENTION

An electronic cigarette comprises an atomizer and a battery pipe, in the prior art, the atomizer and the battery pipe are both serially connected, and thus the body of the cigarette is too long to be carried. Further, the atomizing core component inside the atomizer is not replaceable, the atomizing core component may easily get damaged and dirties after long term use for many times, and the taste of the electronic cigarette is getting bad.

SUMMARY OF THE INVENTION

The technical problem to solve in the invention is to deal with the defects in the prior art that the body is too long and not convenient in carrying, and the atomizing core component is not replaceable, and this invention provides an electronic cigarette, of which a battery pipe is mounted in the atomizer, and an atomizing core component is replaceable.

The technical solution of the invention is as follows: an electronic cigarette is provided, comprising an atomizer and a battery pipe, with an end of the atomizer connected to a sucking mouth component; a battery chamber is configured in the atomizer, and the battery pipe is fixedly inserted in the battery chamber; an atomizing component is also mounted in the atomizer, and the atomizing core component is detachably configured between the battery pipe and the sucking mouth component.

In the electronic cigarette of the invention, the atomizer comprises sleeves, including a first sleeve and a second sleeve axially extending along the opposite direction of the first sleeve; the sucking mouth component is mounted at an end of the second sleeve, the end is far away from the first sleeve.

In the electronic cigarette of the invention, a tar storing chamber for storing smoke tar is encircled by both an outer surface of the battery chamber and an inner surface of the sleeves, and a lid is mounted under the tar storing chamber.

In the electronic cigarette of the invention, the first and second sleeves are formed by integral forming; the lid and the first sleeve are detachably connected.

In the electronic cigarette of the invention, the lid is connected with the first sleeve by threaded connection or interference fitting.

In the electronic cigarette of the invention, the first sleeve and the second sleeve are detachably connected; the lid and the first sleeve are integrally formed.

In the electronic cigarette light of the invention, the first sleeve is connected with the second sleeve by way of threaded connection or interference fitting.

In the electronic cigarette of the invention, both the connections between the first and second sleeves and between the lid and the first sleeve are detachable. Both the connections between the first and second sleeves and between the lid and the first sleeve are by way of threaded connection or interference fitting.

In the electronic cigarette of the invention, a seal sleeve is configured between the sucking mouth component and the atomizing core component, and the seal sleeve is mounted around the outside of the atomizing core component, and the upper part of the seal sleeve is tightly attached to the lower part of the sucking mouth component.

In the electronic cigarette of the invention, a first connector is configured on the lower end of the atomizing core component, and a upper electrode is inserted into the lower part of the first connector, and the lower part of the first connector is detachably connected to the upper part of the battery chamber. In the electronic cigarette of the invention, a battery is fixed in the middle of the battery pipe, an inhalation sensor is mounted in the lower part of the battery pipe, and a battery lid is fixed to the bottom of the battery pipe;

A gap is determined from each of the battery and inhalation sensor to the inner surface of the battery pipe, and at least a second through hole is defined in the battery lid.

In the electronic cigarette of the invention, a magnet is fixed on the upper part of the battery pipe, and via the attraction between the magnet and the battery chamber, the battery pipe is connected to the atomizer; a lower electrode runs through the magnet, and the lower electrode is attached to the upper electrode.

In the electronic cigarette of the invention, a lower electrode is inserted in the upper part of the battery pipe, and the upper electrode is attached to the lower electrode; a first connecting part is protruded on one side of the battery lid, the side is facing the sucking mouth component, a second connecting part is protruded on one side of the lid, the side is far away from the first sleeve, and the first connection part and the second connecting part are connected by way of threaded connection, so as to realize the connection between the battery pipe and the atomizer.

In the electronic cigarette of the invention, the sucking mouth component, the seal sleeve, the atomizing core component, the upper electrode and the lower electrode are all of hollow structure and communicated with each other, and forms an airflow path together with the gap as well as the second through hole.

In the electronic cigarette of the invention, the gap is provided with a width of 0.1-10 mm.

In the electronic cigarette of the invention, the area of second through hole is 2-7 mm$^2$.

By implementing the electronic cigarette of the present invention, following advantages may be obtained: with at least one connection of those between the first and second sleeves and between the lid and the sleeves to be configured as detachable, the atomizing core component can be removed from the sleeves, thus facilitating the replacement of the atomizing core. Further, by inserting the battery pipe into the atomizer, the whole length of the electronic cigarette is reduced, and thus convenient in carrying.

BRIEF DESCRIPTION OF THE DRAWINGS

The present invention will be further described with reference to the accompanying drawings and embodiments in the following, in the accompanying drawings.

DETAILED DESCRIPTION OF THE PREFERRED EMBODIMENT

To make the objective, technical solution and advantages of the invention more clearly understood, the invention is to be further described with reference to the accompanying drawings and embodiments. It should be acknowledged that the embodiments are configured to interpret the invention, and shall not be construed as limiting the invention.

Figure 1:
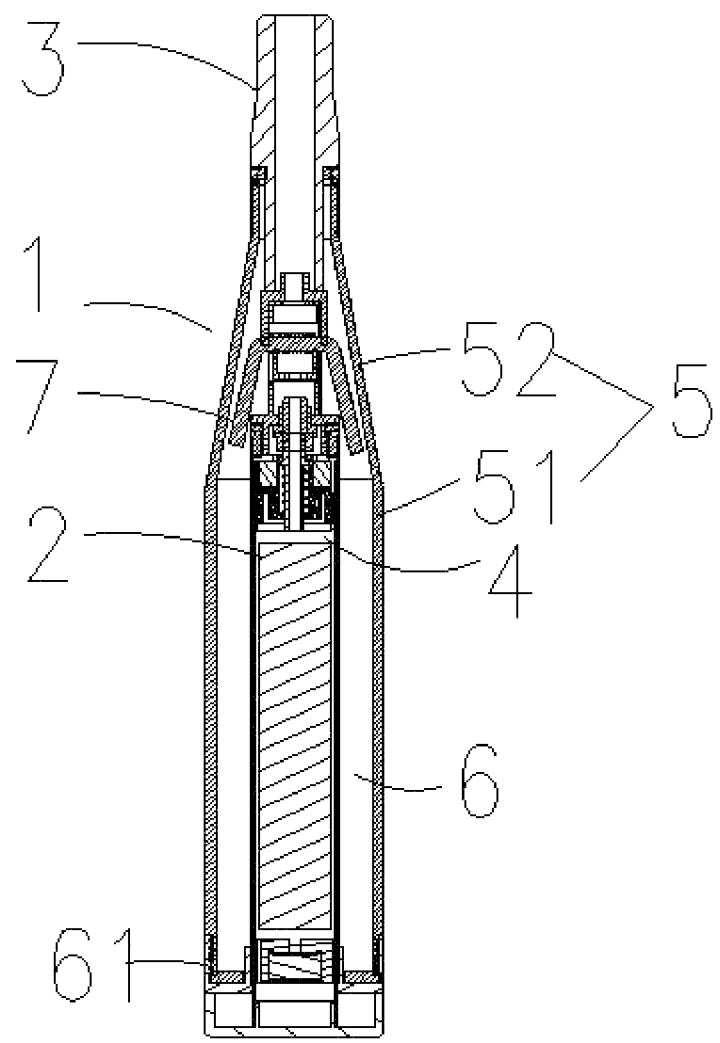
FIG. 1 illustrates an inner structure view of the electronic cigarette in accordance with a first preferable embodiment of the present invention.
Figure 2:
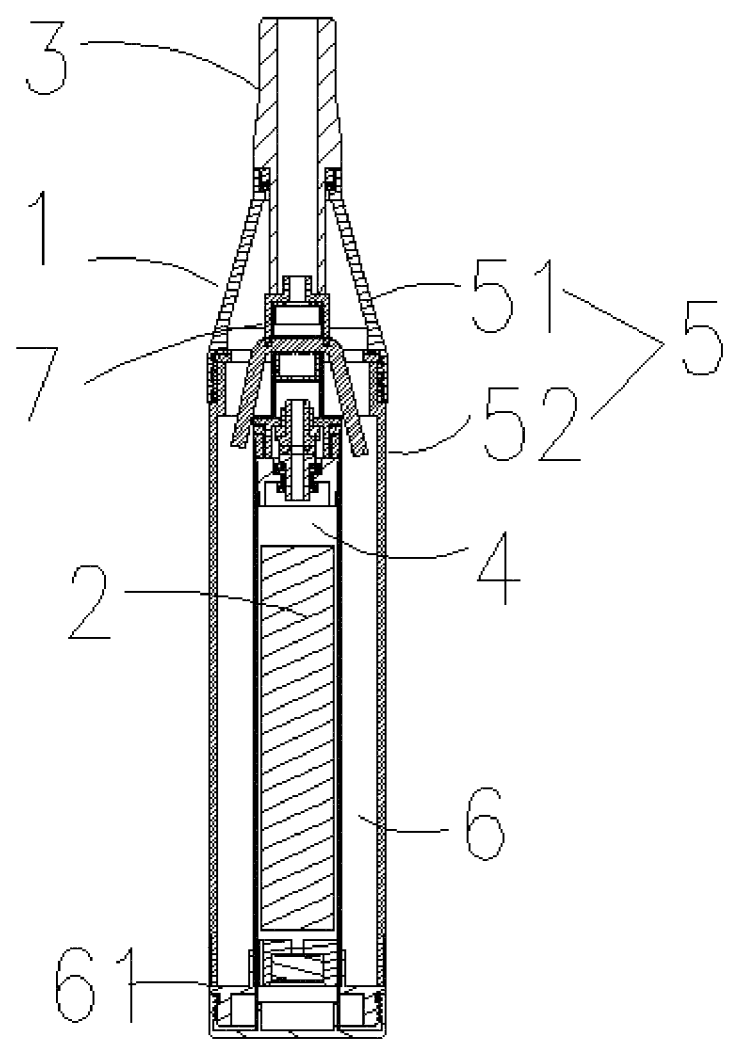
FIG. 2 illustrates an inner structure view of the electronic cigarette in accordance with a second preferable embodiment of the present invention.

Referring to FIG. 1 to 2, the present invention relates to an electronic cigarette, comprising an atomizer 1 and a battery pipe 2, a sucking mouth component 3 is fixed on an end of the atomizer 1, a battery chamber 4 is configured in the atomizer 1, and the battery pipe 2 is inserted fixedly in the battery chamber 4; an atomizing core component 7 is also mounted in the atomizer 1, and the atomizing core component 7 is detachably mounted between the battery pipe 2 and the sucking mouth component 3.

the atomizer 1 comprising sleeves 5, including a first sleeve 51 and a second sleeve 52 axially extending along the opposite direction of the first sleeve 51, and the sucking mouth component 3 is mounted on an end of the second sleeve, the end is far away from the first sleeve 51.

Specifically, the first sleeve can be either cylinder-shaped or taper-shaped, and the second sleeve 52 can be a frustum axially extending along the opposite direction of the first sleeve 51 with its diameter gradually decreasing, or can be a cylinder extending along the opposite direction of the first sleeve 51. A tar storing chamber 6 for storing smoke tar is encircled by both an outer surface of the battery chamber 4 and an inner surface of the sleeves 5, and a lid is mounted under the tar storing chamber 6.

To fulfill the configured atomizing core component 7 being detachable in the atomizer 1, following means can be adopted.

(1) The first sleeve 51 and second sleeves 52 are integrally formed; the lid 61 and the first sleeve 51 are detachably connected.

(2) The first sleeve 51 and the second sleeves 52 are detachably connected, and the first sleeve 51 and the lid 61 are integrally formed.

(3) Both connections between the first sleeve 51 and the second sleeves 52 and between the lid 61 and the first sleeve 51 are detachable.

With at least one connection of those between the first sleeve 51 and the second sleeves 52 and between the lid 61 and the first sleeve 51 to be configured as detachable, the atomizing core component 7 can be removed from the sleeves; when removing the atomizing core component 7 from the upper part of the atomizer 1, the connection between the first sleeve 51 and the second sleeve 52 is configured as detachable, by removing the first sleeve 51 firstly then taking out the atomizing core component 7; when removing the atomizing core component 7 from the lower part of the atomizer 1, the connection between the lid 61 and the first sleeve 51 may be configured as detachable, and with the battery chamber 4 to be removed after the lid being detached from the first sleeve 51, thus the atomizing core component 7 can be removed simultaneously (the top, lower part or the upper end, lower end are all defined as watching from the top down definition from the sucking mouth component 3 to the lid 61 direction in the present invention).

When the first sleeve 51 is detachably connected with the second sleeve 52, as shown in FIG. 2, the connection is obtained by threaded connection or interference fitting. When it is threaded connection, to avoid tar exuding from the sleeves 5, a seal gasket is needed to be mounted at the connecting position. When outer screw thread is configured on the first sleeve 51, internal screw thread is defined on the second sleeve, and the connection can be obtained by screwing the internal and outer screw thread. Herein, a seal gasket is mounted at an end of the connection position configured with internal screw thread, so as to prevent the tar from exuding from the sleeves 5. Likewise, the internal screw thread can be defined on the first sleeve 51, and the outer screw thread be configured on the second sleeve 52, so as to obtain the threaded connection.

Figure 8:
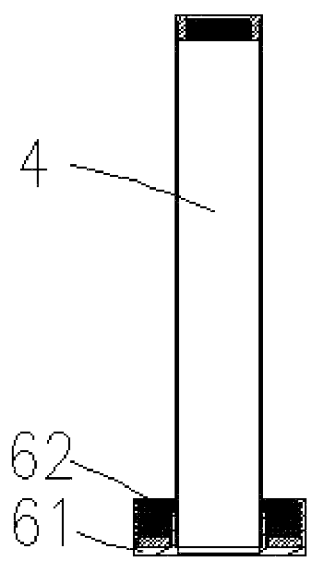
FIG. 8 illustrates a structure of a battery chamber in accordance with a preferable embodiment of the present invention
Figure 9:
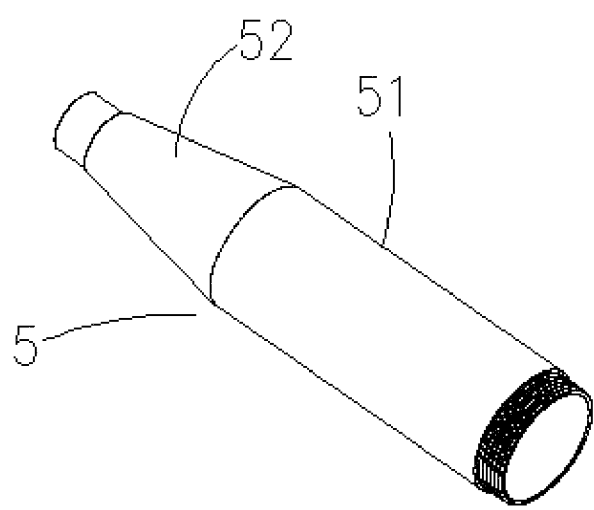
FIG. 9 illustrates a structure of a sleeve connected with the battery chamber of FIG. 8.

The same as the detachable connection between the first and second sleeves 51-52, when the lid 61 is detachably connected with the sleeves 5, the lid 61 in FIG. 8 and the first sleeve 51 in FIG. 9 are connected, by screwing or interference fitting. When it is screwing connection, to avoid tar exuding from the connecting position, a seal gasket is needed to be mounted at the connecting position. Also, a seal gasket is mounted at an end of the connection position configured with internal screw thread. The outer screw thread can be defined on the lid, and the internal screw thread can be defined on the first sleeve 51, and also the internal screw thread can be defined on the lid, while the outer screw thread can be defined on the first sleeve 51.

Figure 3:
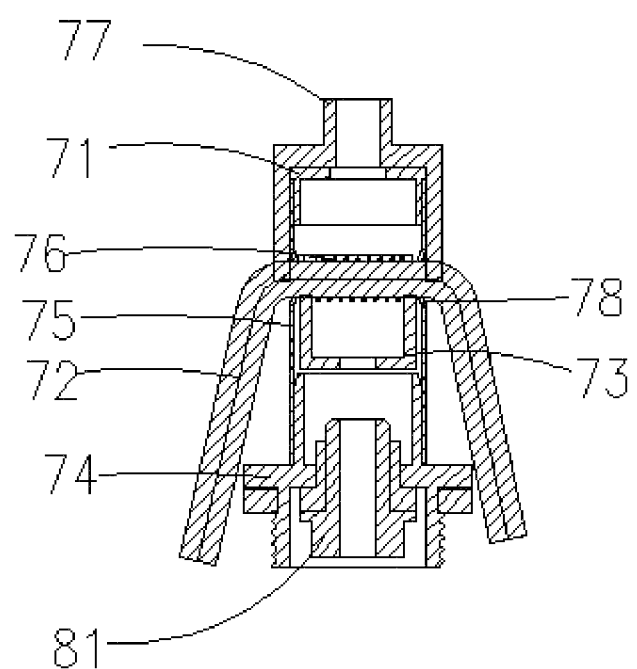
FIG. 3 illustrates a structure of an atomizing core component of the electronic cigarette of the present invention.

As shown in FIG. 3, the atomizing component 7, from the top down, comprises an atomizing cover 71, an atomizing core 72, an atomizing base 73, and a first connector 74, and also comprises an atomizing pipe 75. The lower part of the atomizing cover 71, the whole atomizing base 73, and upper part of the first connector 74 are all inserted into the atomizing pipe 75; a upper electrode 81 is inserted into the lower part of the first connector; a pair of first through holes 78 are correspondingly defined on both sides of the atomizing pipe 75, and the atomizing core 72 is supported on above of the atomizing base, with both ends of the atomizing core 72 running through the first through holes 78, and extending into the smoke tar storing chamber 6. The outer surface of the atomizing core 72 is closely covered with heating wires 76.

Figure 4:
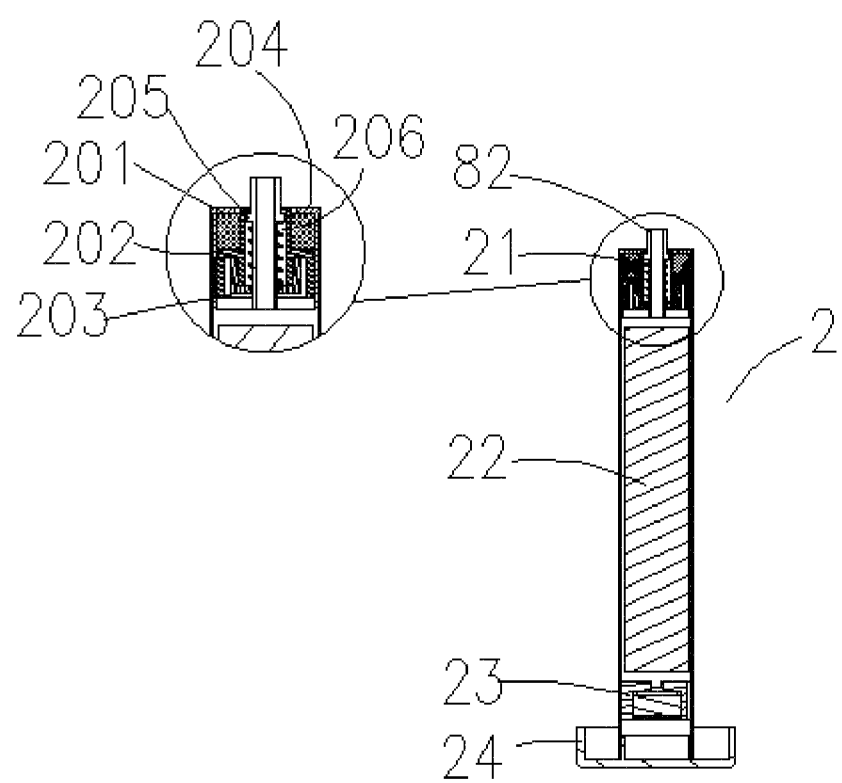
FIG. 4 illustrates an inner structure of a battery pipe of the electronic cigarette in accordance with the first preferable embodiment of the present invention.

As shown in FIG. 1 and FIG. 4, a seal sleeve 77 is also configured between the suction mouth component 3 and the atomizing core component 7, and the seal sleeve 77 is configured to fit over the atomizing core component 7; upper part of the seal sleeve 77 is tightly attached to the lower part of the sucking mouth component 3.

Specifically, the seal sleeve 77 is fitting over outside of the atomizing pipe 75, and the seal sleeve 77 extends to the first through holes 78, thus a part of the first through holes 78 being covered. With a part of the first though holes being covered by the seal sleeve 77, and the atomizing core being extruded, the rest area of the first through holes 78 can be just suitable for the atomizing core to run through, and there could be no gap for the tar to flow in. It should be understood that the covered area of the first through holes 78 may relate to the section area of the atomizing core, and an area to keep for the atomizing core to run through will do.

Specifically, the way for the supporting base to support the atomizing core 72 is that, by defining a pair of notches corresponding to the first through holes 78 in the radial direction on the supporting base, the atomizing core 72 is mounted on the notches.

As shown in FIGS. 1 to 3, the lower part of the first connector 74 is detachably connected with the upper part of the battery chamber 4, specifically by way of threaded connection. Understandably, the first connector can be connected with the battery chamber 4 by way of interference fitting or snap fitting. When it is threaded connection, a seal gasket is needed to be mounted at the connecting position to avoid tar flowing into the battery chamber from the connecting position. The lower part of the first connector can be configured with outer screw threads, and internal screw threads are defined on the upper part of the battery chamber 4; also, the internal screw thread can be defined on the lower part of the first connector 74, and the outer screw threads be configured on the upper part of the battery chamber 4.

As it is mentioned above, an upper electrode 81 is inserted into the lower part of the first connector 74. Specifically, a second insulated covering is mounted between the upper electrode 81 and the first connector 74. The second insulated covering would not just work for insulation, but also involves elasticity. During the assembling, with the second insulated covering 208 being extruded, it can be obtained that the upper electrode 81 can be fixed with the first connector 74.

Figure 7:
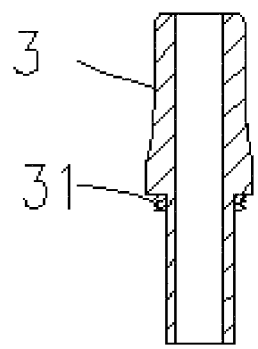
FIG. 7 illustrates a structure of a sucking mouth component of the invention.

As shown in FIG. 1, FIG. 2, and FIG. 7, in the present invention, the sucking mouth component 3 is connected with the second sleeve 52 by the way of threaded connection. The sucking mouth component 3 comprises a root, on which a fillet of screw 31 defined with outer screw threads is fitting over. The second sleeve is defined with internal screw threads, thus the threaded connection being obtained. Understandably, to avoid the tar exuding, a seal gasket is needed to be mounted at the connecting position of the sucking mouth component 3 and the second sleeve 52.

Figure 5:
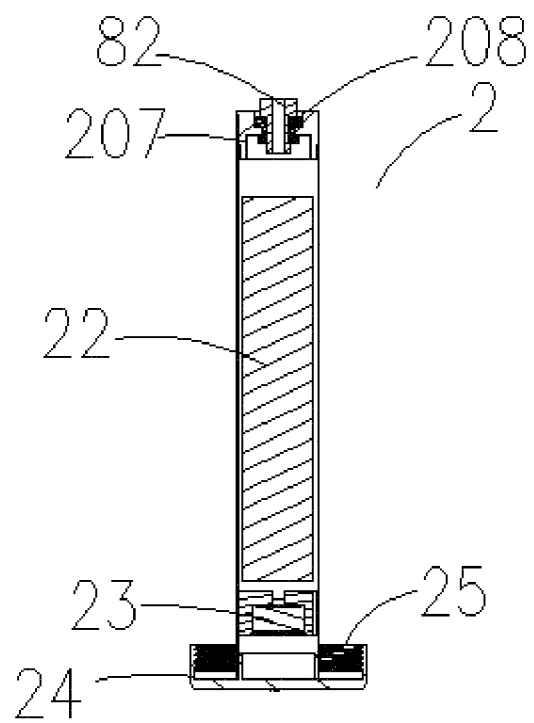
FIG. 5 illustrates an inner structure of a battery pipe of the electronic cigarette in accordance with the second preferable embodiment of the present invention.

With the sucking mouth component 3 detachably connected to the second sleeve 52, when the smoke tar is deficient, the sucking mouth component 3 could be removed, and the tar can be supplemented from the opening of the second sleeve 52, thus convenient in using. Understandably, the first sleeve 51 and the second sleeve 52 can be transparent, and through the transparent first sleeve 51 and second sleeves 52, it could be convenient for observing the smoke tar amount, As shown in FIG. 4 and FIG. 5, a battery is fixed in the middle of the battery pipe, an inhalation sensor is mounted in the lower part of the battery pipe 2, and a battery lid 24 is fixed to the bottom of the battery pipe 2; a gap is determined from each of the battery 22 and inhalation sensor 23 to the inner surface of the battery pipe 2, and at least a second through hole (not shown) is defined in the battery lid 24.

The battery pipe 2 can be connected with the atomizer 1 through magnetic connection or threaded connection. Below is a first embodiment that the battery pipe 2 is magnetically connected with the atomizer 1.

As shown in FIG. 1 and FIG. 4, in this instance, a magnet 21 is fixed on the upper end of the battery pipe 2, and via the attraction between the magnet 21 and the battery chamber 4, the battery pipe 2 is connected to the atomizer 1. Specifically, this connection is obtained by the attraction between the magnet 21 and the connecting position of the first connector 74 and the battery chamber 4. A lower electrode 82 runs through the middle of the magnet 21, and the upper electrode 81 is attached to the lower electrode 82.

Specifically, one way of fixing the magnet 21 to the upper end of the battery pipe 2 is that, by mounting a first fixing sleeve 201 on the top of the magnet 21, in the fixing sleeve, configuring a first insulated covering 202 interference fitting with the first fixing sleeve 201, and a hollow insulated sleeve being embedded in the middle of the first insulated covering 202, and thus a space for exactly accepting the magnet 21 is formed by lateral sides of the insulated sleeve and the top of the first fixing sleeve 201, and in this case the magnet 21 is fixed. An electrode lid 203 is fixed on lower end of the insulated sleeve. In this instance, the first insulated covering 202 works for insulation as well as fixing; the electrode lid 203 is interference-fitting with lower part of the insulated sleeve; the lower electrode runs through the first fixing sleeve 201, the first insulated covering 202 and the electrode lid 203 and gets fixed.

As shown in FIG. 3, the lower electrode 82 is fixed into the battery pipe 2 by the way of configuring a first flange 204 in the upper part of the insulated sleeve, and a second flange 205 on the upper part of the lower electrode 82, in which case the second flange 205 is configured to be underneath and attach to the first flange 204, and a spring 206 is configured between the second flange 205 and the electrode lid 203. By keeping the spring 206 compressed, the lower electrode 82 can be fixed in the battery pipe 2.

When the battery pipe 2 is magnetically connected with the atomizer 1, in the lower part of the battery pipe 2, there is no need for configuring any other connecting device to connect with the atomizer 1, for the battery lid 24 in the bottom can make it available to remove and replace the battery 22. The battery lid is connected with the battery pipe 2 by interference fitting or any other way, such as screwing or snap-fitting.

Below is a second embodiment that the battery pipe 2 is connected with the atomizer by way of threaded connection, and particularly by the threaded connection between the tar storing chamber 6 and the battery pipe 2.

As shown in FIG. 2 and FIG. 5, in this instance, there is no magnet 21 on top of the battery pip2, and instead a second fixing sleeve 207 is mounted on the upper end of the battery pipe 2, and the lower electrode 82 is inserted into the second fixing sleeve 207.

The way to connect the lower electrode 82 to the top of the battery pipe 2 is that, by connecting the top of the battery pipe 2 to the second fixing sleeve 207 via interference fitting, inserting the lower electrode 82 into the second fixing sleeve 207, and configuring a insulated ring between the second fixing sleeve 207 and the lower electrode 82, the insulated ring is mounted to the outer side of the lower electrode 82 and gets compressed, thus fixing the lower electrode 82 in the second sleeve 207.

Figure 6:
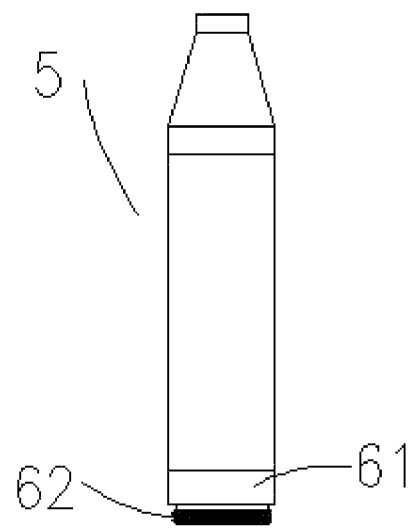
FIG. 6 illustrates a structure of a sleeve connection-fitting with the battery pipe in FIG. 5.

The smoke tar chamber and the battery pipe are configured to be connected by way of threaded connection. The lid 61 in the FIG. 6 and the battery lid 24 in FIG. 5, is connected by the way of threaded connection.

A first connecting part 25 is protruded on one side of the battery lid 24, the side is facing the sucking mouth component 3, a second connecting part 62 is protruded on one side of the lid 61, the side is far away from the first sleeve 51, and the first connecting part 25 and second connecting part, 62 are threaded connection, so as to obtain the connection between the battery pipe 2 and the atomizer 1.

Specifically, the section of the lower end of the battery pipe 2 involves a symmetrical structure, and in this structure, internal screw threads (i.e., the first connecting part 25) are defined in the inner surface. The lid 61 extends downward to form the connecting part 62, on which external screw threads are defined, and by inserting the second connecting part 62 into the hooked structure and threaded connection, the battery pipe and the atomizer get connected.

In the above-mentioned two embodiments of magnetic connection and threaded connection, the sucking mouth 3, the seal sleeve 77, the atomizing component 7, upper electrode 81 and the lower electrode 82 are all in a hollow structure and communicated with each other, and together with the gap and the second through hole, an airflow path for is formed, to provide passage for air during smoking Understandably, when the width of the gap may be 0.1-10 mm, and the area of the through hole be 2-6 mm2, air could smoothly run through the airflow path In conclusion, since it is detachable to at least one of the connections between the first sleeve 51 and the second sleeve 52 and between the connection of lid 61 and the first sleeve 51. Thus the atomizing core component 7 can get removed out from the sleeve, so as to get the atomizing core 72 replaced conveniently. Also, by inserting the battery pipe 2 into the atomizer 1, the whole length of the electronic cigarette is reduced, thus convenient in carrying.

While the present invention has been described with reference to preferred embodiments, it will be understood by those skilled in the art that various changes may be made and equivalents may be substituted without departing from the scope of the present invention. Thus, the present invention will not be limited by the specific embodiments disclosed, but should include all the embodiments within the scope of the appended claims.

What is claimed is:

1. An electronic cigarette, comprising an atomizer and a battery pipe, a sucking mouth component connected with an end of the atomizer, characterized in that a battery chamber is mounted in the atomizer, and the battery pipe is fixedly inserted in the battery chamber; an atomizing core component is mounted in the atomizer, and is detachably configured between the battery pipe and the sucking mouth component; wherein the atomizer has sleeves, including a first sleeve and a second sleeve axially extending along the opposite direction of the first sleeve; the sucking mouth component is mounted at an end of the first sleeve, the end is opposite from the second sleeve; wherein a tar storing chamber for storing smoke tar encircles an outer surface of the battery chamber and is encircled by an inner surface of the sleeves, and a lid is mounted under the tar storing chamber; wherein a seal sleeve is configured between the sucking mouth component and the atomizing core component, and the seal sleeve is mounted around an outside of the atomizing core component, and an upper part of the seal sleeve is tightly attached to a lower part of the sucking mouth component; wherein a first connector is configured on a lower end of the atomizing core component, and an upper electrode is inserted into a lower part of the first connector, and the lower part of the first connector is detachably connected to an upper part of the battery chamber; wherein a battery is fixed in the middle of the battery pipe.

2. The electronic cigarette of claim 1, wherein the first sleeve and the second sleeve are formed by integral forming; the lid and the first sleeve are detachably connected.

3. The electronic cigarette of claim 2, wherein the lid is connected with the first sleeve by way of threaded connection or interference fitting.

4. The electronic cigarette of claim 1, wherein the first sleeve and the second sleeve are detachably connected; the lid and the first sleeve are integrally formed.

5. The electronic cigarette of claim 4, wherein the first sleeve is connected with the second sleeve by way of threaded connection or interference fitting.

6. The electronic cigarette of claim 1, wherein both the connections between the first sleeve and second sleeve and between the lid and the first sleeve are detachable.

7. The electronic cigarette of claim 6, wherein both the connections between the first sleeve and the second sleeves and between the lid and the first sleeve are by way of threaded connection or interference fitting.

8. The electronic cigarette of claim 1, wherein an inhalation sensor is mounted in the lower part of the battery pipe, and a battery lid is fixed to the bottom of the battery pipe; a gap is determined from each of the battery and inhalation sensor to the inner surface of the battery pipe, and at least a second through hole is defined in the battery lid.

9. The electronic cigarette of claim 8, wherein a magnet is fixed on the upper end of the battery pipe, and via the attraction between the magnet and the battery chamber, the battery pipe is connected to the atomizer; a lower electrode runs through the magnet, and the lower electrode is attached to the upper electrode.

10. The electronic cigarette of claim 9, wherein a lower electrode is inserted in the upper end of the battery pipe, and the upper electrode is attached to the lower electrode; a first connecting part is protruded on one side of the battery lid, the side is facing the sucking mouth component, a second connecting part is protruded on one side of the lid the side is opposite from the first sleeve, and the first connecting part and the second connecting part are threaded connection, so as to realize the connection between the battery pipe and the atomizer.

11. The electronic cigarette claim 10, wherein the sucking mouth component, the seal sleeve, the atomizing core component, the upper electrode and the lower electrode are all of hollow structure and communicated with each other, and form an air flow path together with the gap and the second through hole.

12. The electronic cigarette of claim 11, wherein the gap is provided with a width of 0.1-10 mm.

13. The electronic cigarette of claim 11, wherein the area of second through hole is 2-7 mm$^2$.

* * * * *